(12) United States Patent
Brock et al.

(10) Patent No.: US 6,823,736 B1
(45) Date of Patent: Nov. 30, 2004

(54) NONDESTRUCTIVE ACOUSTIC EMISSION TESTING SYSTEM USING ELECTROMAGNETIC EXCITATION AND METHOD FOR USING SAME

(75) Inventors: David W. Brock, San Diego, CA (US); Narayan R. Joshi, Beaumont, TX (US); Stephen D. Russell, San Diego, CA (US); Markham E. Lasher, San Diego, CA (US); Shannon D. Kasa, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/302,320

(22) Filed: Nov. 20, 2002

(51) Int. Cl.[7] ............................................. G01N 29/14
(52) U.S. Cl. ........................................................ 73/587
(58) Field of Search ......................... 73/587, 601, 643; 324/637

(56) References Cited

U.S. PATENT DOCUMENTS

| | | | |
|---|---|---|---|
| 4,543,486 A | * | 9/1985 | Rose ............................ 73/643 |
| 4,562,736 A | * | 1/1986 | Iwasaki et al. ............... 73/587 |
| 4,949,034 A | * | 8/1990 | Imura et al. ................. 324/642 |
| 5,170,666 A | * | 12/1992 | Larsen .......................... 73/643 |
| 5,199,054 A | | 3/1993 | Adams et al. |
| 5,406,500 A | | 4/1995 | Floret |
| 5,526,689 A | | 6/1996 | Coulter et al. |
| 5,621,811 A | | 4/1997 | Roder et al. |
| 5,713,356 A | * | 2/1998 | Kruger ........................ 600/407 |
| 5,825,182 A | | 10/1998 | Nakayama et al. |
| 5,924,986 A | * | 7/1999 | Chandler et al. ........... 600/407 |
| 6,049,411 A | | 4/2000 | Sandhu et al. |
| 6,065,342 A | * | 5/2000 | Kerr et al. .................... 73/587 |

* cited by examiner

*Primary Examiner*—John E. Chapman
(74) *Attorney, Agent, or Firm*—Celia C. Dunham; Michael A. Kagan; Peter A. Lipovsky

(57) ABSTRACT

A nondestructive acoustic emission testing system using electromagnetic excitation, comprises: a) an electromagnetic wave generator for generating electromagnetic waves that stimulate a test sample to generate acoustic energy; b) an acoustic energy sensor for detecting the acoustic energy and generating a first output signal that represents the acoustic energy; and c) a data processor for comparing the output signal with a reference and for generating a second output signal that represents a characteristic of the test sample.

6 Claims, 6 Drawing Sheets

NONDESTRUCTIVE ACOUSTIC EMISSION TESTING SYSTEM USING ELECTROMAGNETIC EXCITATION AND METHOD FOR USING SAME

BACKGROUND OF THE INVENTION

Nondestructive testing (NDT) has proven to be an important technique in quality control and safety testing. An NDT system that employs a probe signal is referenced as an "active system." A well known type of active NDT system uses an ultrasonic probe signal for detecting defects and non-uniformities in structures or layers without destroying or damaging the sample under study. An acoustic transducer generates an ultrasonic probe signal that impinges on a sample under study. A second acoustic transducer receives an acoustic emission signal from the test sample that results from perturbation of the original probe signal due to interfaces, structural changes or defects in the material. Disadvantages of NDT systems that use ultrasonic techniques include complexity in quantitative analysis due to the need to decouple parasitic acoustic signals between the source and the detectors. Acoustic emission (AE) analysis is also used in NDT applications such as: detecting and locating faults in pressure vessels, storage tanks, pipe systems, and also in corrosion processes. Another type of NDT technique employs a "passive system" which uses an acoustic detector but no acoustic excitation source. A disadvantage of a passive system is that it may only be used to estimate the amount of damage in the material or how long a component will last. Another disadvantage of a passive system is that signals are typically smaller because there is no means to increase the level of the stimuli to increase signals. Furthermore, service environments are very noisy and AE signals tend to be very weak, thus signal discrimination and noise reduction are difficult. Another example of an NDT system uses liquid penetrant as a means of inspection. In a liquid penetrant system, a fluorescent or colored dye contrast liquid penetrant is deposited on a test article. The liquid penetrant is allowed to penetrate into the test article by capillary action into any surface defects. Analysis is achieved by illuminating the test article with ultraviolet or visible light to observe fluorescence or image changes. Then the test article is cleaned by use of a solvent. Shortcomings of using a penetrant include the requirement of a multiple step process, incompatibility between the penetrant and or solvent with the test article, containment of excess penetrant liquid, and limited detection of subsurface defects.

Thus, it may be appreciated that a need exists for a nondestructive technique for detecting defects and non-uniformities in structures or layers without destroying or damaging the sample under study which avoids the inherent limitations and difficulties of the prior art.

SUMMARY OF THE INVENTION

A nondestructive acoustic emission testing system using electromagnetic excitation, comprises: a) an electromagnetic wave generator for generating electromagnetic waves that stimulate a test sample to generate acoustic energy; b) an acoustic energy sensor for detecting the acoustic energy and generating a first output signal that represents the acoustic energy; and c) a data processor for comparing the output signal with a reference and for generating a second output signal that represents a characteristic of the test sample.

BRIEF DESCRIPTION OF THE DRAWINGS

Throughout the several views, like elements are referenced using like references.

DESCRIPTION OF THE PREFERRED EMBODIMENT

Figure 1:
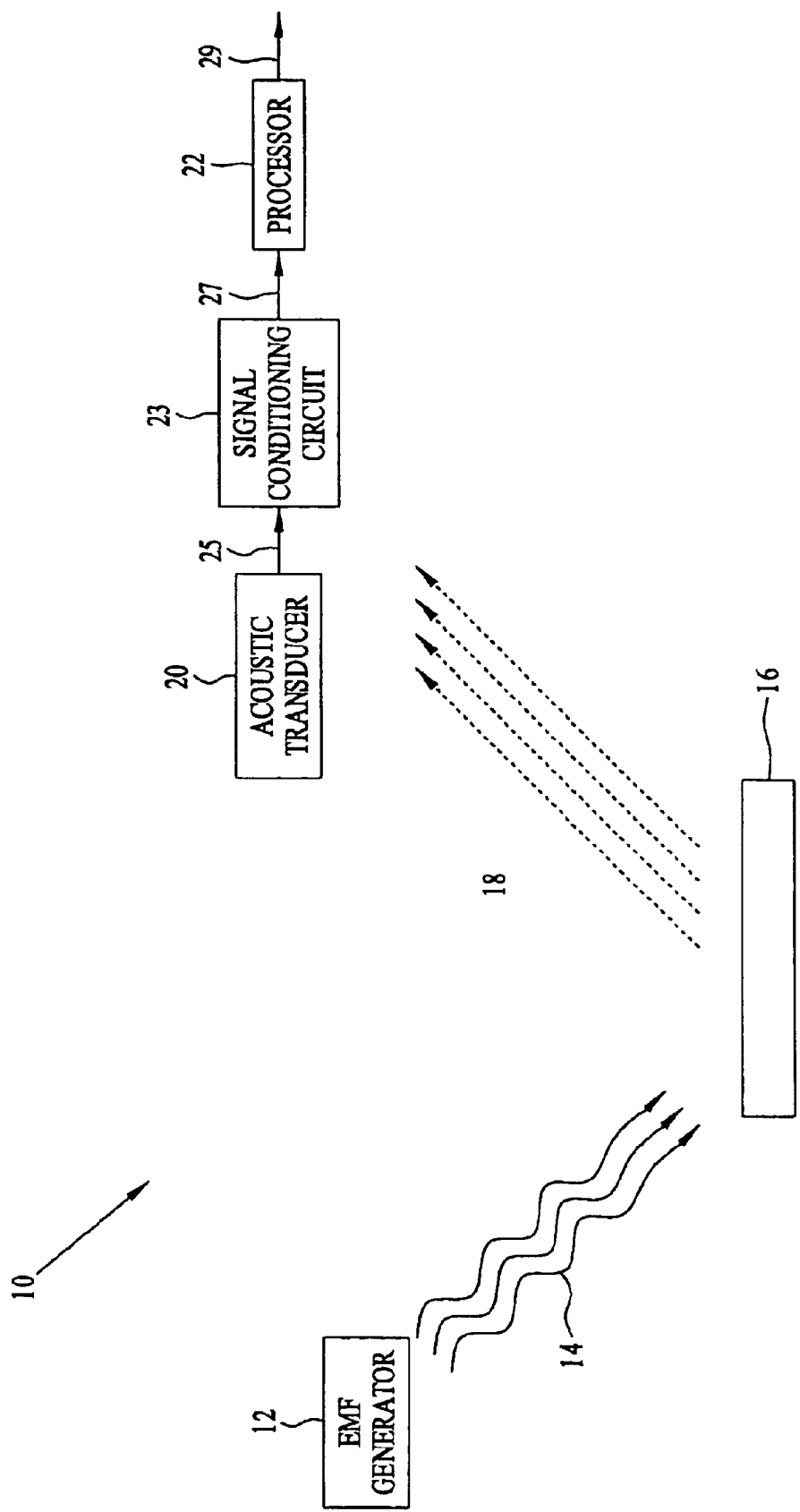
FIG. 1 shows an embodiment of a nondestructive acoustic emission testing system using electromagnetic excitation wherein the acoustic energy sensor is positioned remotely from the test sample.

Referring to FIG. 1 there is shown an embodiment of a nondestructive acoustic emission testing system 10 that uses electromagnetic excitation to stimulate acoustic emissions from a test sample. System 10 includes an electromagnetic wave generator 12, an acoustic energy transducer 20, and a data processor 22. Electromagnetic wave generator 12 generates electromagnetic energy 14 for stimulating a test sample 16 to generate an acoustic energy signal 18. In general, acoustic vibrations of a structure or test sample 16 with damage or defects differ greatly from those of a structure that either is not damaged or has no defects. Moreover, the relative changes in the characteristics of acoustic energy signal 18 over time may be used to estimate changes in the properties (for example structural integrity, corrosion, and the like) of the test sample 16. The frequency content of the acoustic energy signal 18 may be greatly affected by the characteristics of the test sample 16, which may cause attenuation, reflections, and/or mode conversions of the acoustic energy signal 18. By way of example, the test sample 16 may include electron tubes, aircraft structures, metallic structures, engine components, turbine blades, and any other type of structure that vibrates or emits acoustic energy when irradiated with electromagnetic radiation.

Figure 2:
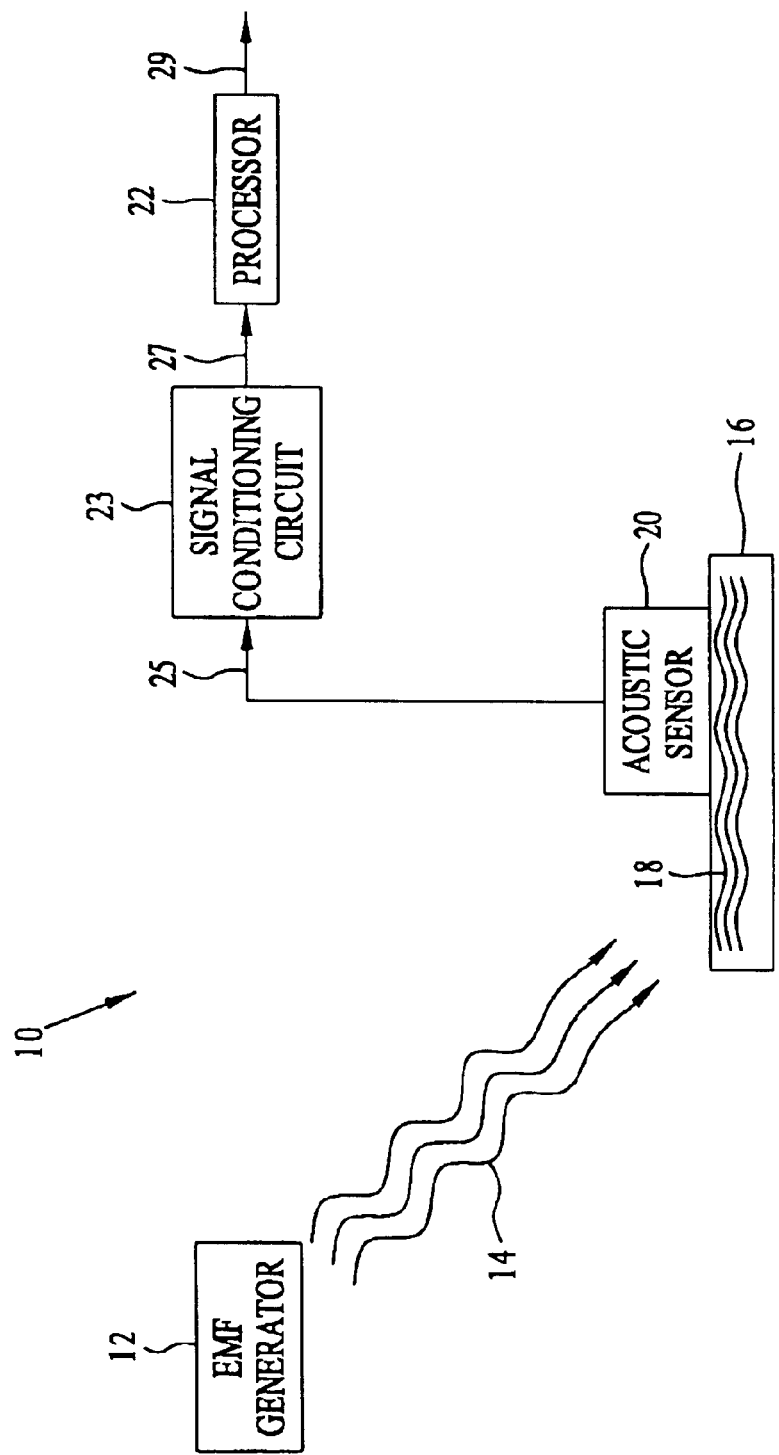
FIG. 2 shows an embodiment of a nondestructive acoustic emission testing system using electromagnetic excitation wherein the acoustic energy sensor is mounted on the test sample.

Still referring to FIG. 1, acoustic energy transducer 20 maybe positioned remotely from the test sample 16 so that as acoustic energy signal 18 propagates through an acoustic propagating medium (or couplant) such as air or water, signal 18 is detected by acoustic energy transducer 20. In another embodiment, the acoustic energy transducer 20 may be mounted directly onto test sample 16, as shown in FIG. 2. In response to detecting acoustic energy signal 18, acoustic energy transducer 20 generates a first output signal 25 that represents the waveform of the acoustic energy signal 18. Then, in response to receiving the first output signal 25, a data processor 22 provides a second output signal 29 that represents a structural characteristic of the test sample. By way of example, acoustic emission transducer 20 may be a piezoelectric transducer such as Physical Acoustics model R50, R80, S9208 or Digital Wave Corporation model B1025. The frequency response of these sensors is: 100 to 700 kHz; 200 to 1000 kHz; 20 to 1000 kHz; and 1 to 1.5 kHz, respectively. However, it is to be understood that the acoustic emission testing system 10 may employ acoustic emission transducers having a detection sensitivity anywhere in the range of about 1 kHz to 1000 kHz. The voltage output signal 25 from 6 acoustic emission transducer 20 may be subjected to suitable signal processing, such as amplification and/or filtering by signal conditioning circuit 23 which transforms first output signal 25 into a signal conditioned output signal 27.

In general, processor 22 may implement mathematical techniques using suitable software routines that compares the waveform characteristics of output signal 27 with a reference. The reference represents the characteristics of acoustic energy signal 18, and hence signal 25, that result when test sample 16 is irradiated with energy 14, emits acoustic energy signal 18, and is in an undamaged and/or non-defective state. In response to analyzing output signal 27, processor 22 may generate an output signal 29 that represents a characteristic of test sample 16. Deviations between the waveform characteristics of output signal 27 and the reference may be used to determine the condition of test sample 16, and for example, determine whether test sample 16 has incurred a structural change that may be indicative of damage. By way of example, processor 22 may implement any of several mathematical techniques for determining the structural characteristics of test sample 16 using a suitable software program such as the Integrated Condition Assessment System (ICAS) by the IDAX Corporation for scaling or normalizing data, performing trend analysis, and the like.

One example of a mathematical technique that may be implemented by processor 22 is the integration of values representing waveform of signal 27 over a period of time, where signal 27 represents both the waveform of acoustic energy signal 18 and the structural characteristic(s) of the test sample 16. Sufficient deviations between the integrated values obtained from signal 27 and the reference may be used to indicate that test sample 16 is defective and/or damaged. It is to be understood that the reference may have a single value or consist of a set of values. In another embodiment, processor 22 may be employed to implement a mathematical technique using a suitable software routine that identifies and compares the maximum amplitude of signal 27 with the maximum amplitude of a reference value that corresponds to an undamaged and/or non-defective test sample 16. In such an analysis, the reference value represents the maximum amplitude of signal 27 that is generated by acoustic energy transducer 20 when test sample 16 is irradiated by energy 14 and is in an undamaged and/or non-defective state.

Another example of a mathematical technique for analyzing the structural characteristics of test sample 16 is a fast Fourier transform (FFT) of the characteristics of signal 27, and hence the waveform characteristics of acoustic energy signal 18, to identify frequency components that could be characteristic of defects or changes in the structural characteristics of test sample 16. Yet another example of a mathematical technique that may be employed to assess the structural characteristics of test sample 16 may use the slope of the onset of acoustic energy signal 18. Changes in the slope over time may be correlated with changes in the condition or structural characteristics of the test sample 16.

Processor output signal 29 may be a single number representing, for example the integrated value of acoustic energy signal 18, or the maximum value of acoustic energy signal 18, which may subsequently be used for trend analysis. Alternatively, the output signal 29 may be the FFT of a representation of acoustic energy signal 18 which may be displayed on a computer monitor for visible identification or monitoring. In another embodiment, the values of the output signal 29 may be a compilation of data arranged in a two-dimensional or three-dimensional rendition on a display.

Electromagnetic wave generator 12 may be implemented as a magnetron, traveling wave tube, klystron, a solid-state device, or any other type of device that generates electromagnetic radiation or waves. Preferably, electromagnetic energy 14 may be in the microwave or radio frequency region of the electromagnetic spectrum (100 kHz to 100 Ghz), and be pulsed or continuous. Pulsed energy may be employed to impart high peak intensities to maximize signals for the time of arrival techniques, or used with low duty cycle to avoid damage to samples which can not withstand continuous irradiation. Examples of suitable acoustic energy sensors include piezoelectric devices, surface acoustic wave devices, micro-electro mechanical systems (MEMS), and any other type of transducer that generates an output signal representing the waveform of a detected acoustic energy signal.

Figure 3:
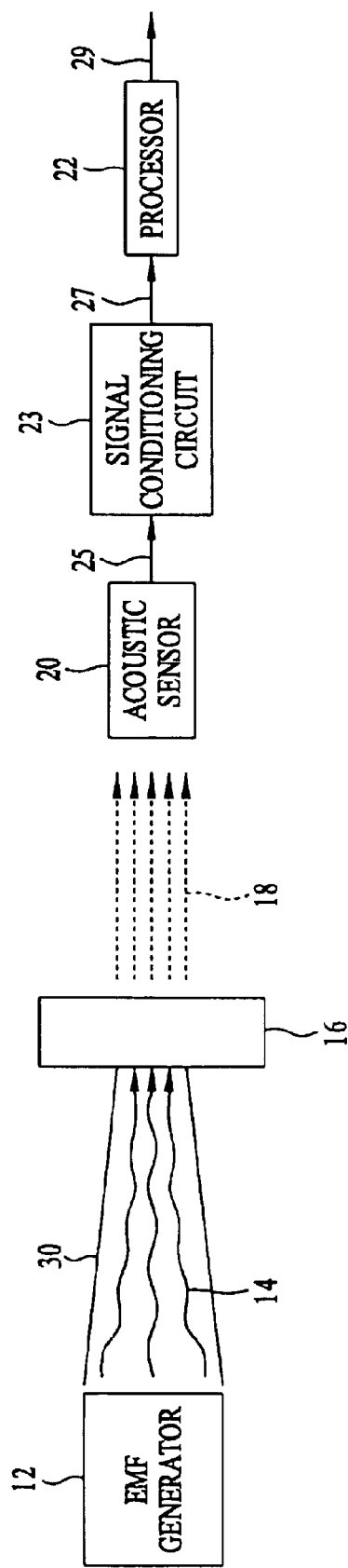
FIG. 3 shows an embodiment of the nondestructive acoustic emission testing system of FIG. 1 wherein electromagnetic energy is directed through a waveguide.
Figure 4:
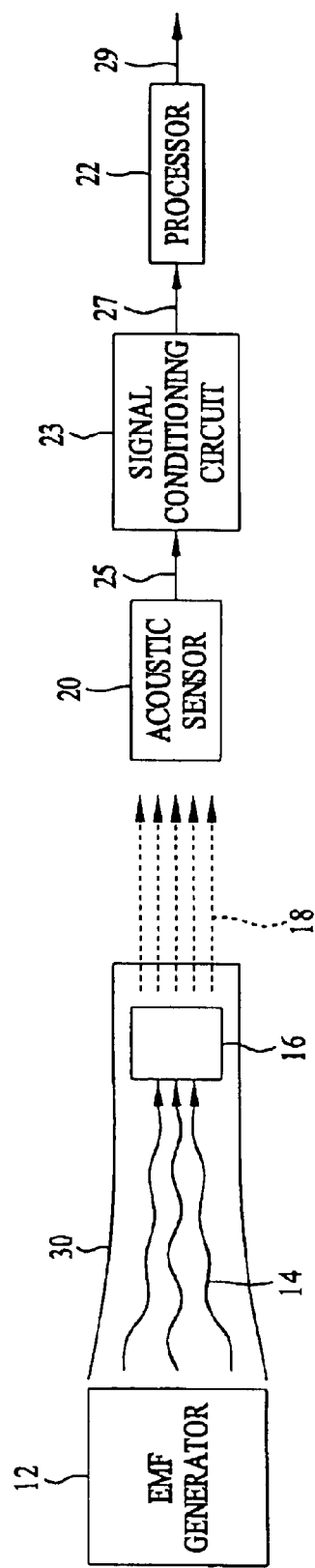
FIG. 4 shows an embodiment of the nondestructive acoustic emission testing system of FIG. 1 wherein a test sample is positioned inside a waveguide.

As shown in FIG. 3, electromagnetic energy 14 may be propagated through a waveguide 30 to direct electromagnetic energy 14 onto the test sample 16. Also, as shown in FIG. 4, the test sample 16 may be placed inside or enclosed by the waveguide 30 in order to direct, and thereby concentrate, the electromagnetic irradiation flux to which the sample 16 is subjected.

Figure 5:
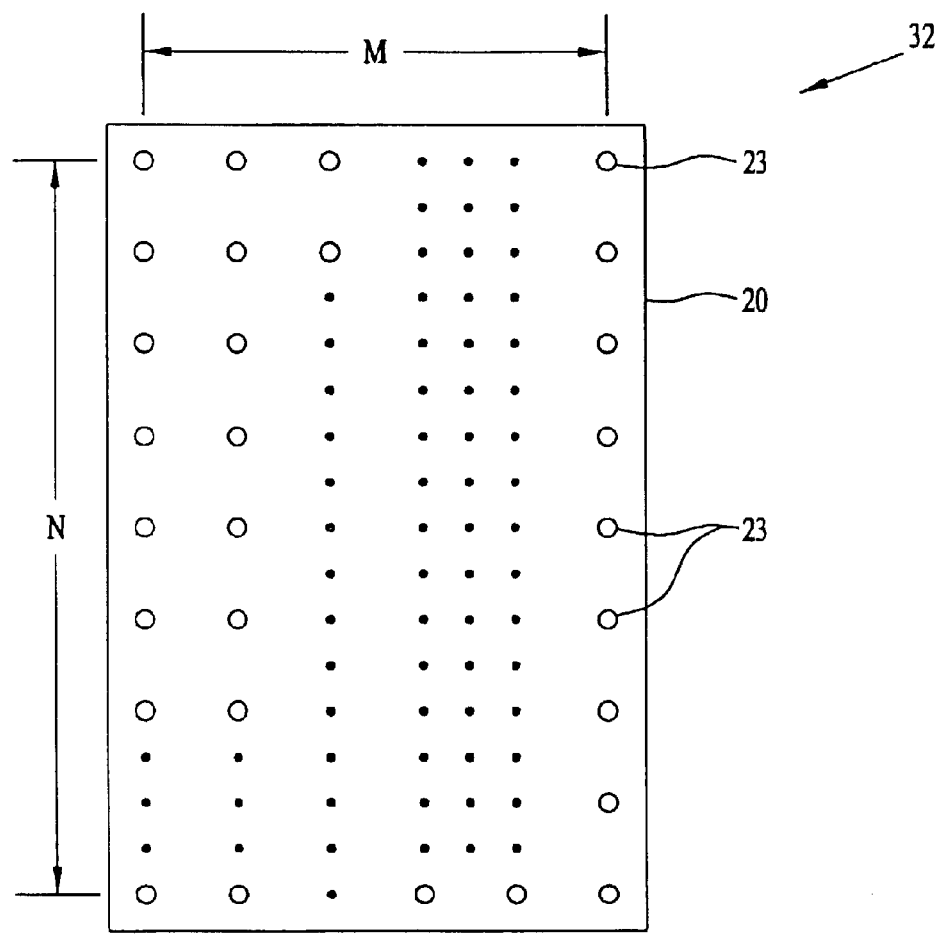
FIG. 5 shows an embodiment of the nondestructive acoustic emission testing system of FIG. 1 wherein the acoustic energy sensor is configured as an array of acoustic transducers.

In FIG. 5, acoustic energy transducer 20 may be implemented as an array 32 of acoustic transducers to facilitate two-dimensional (2D) acoustic imaging of the test sample 16. For example, array 32 may be implemented as an M×N array of transducers 23, where M and N each are positive integers. However, it is to be understood that array 32 may be a circular array or be configured in an array having any other shape or pattern that provides two or three dimensional spatial resolution. Each transducer 23 in array 32 may detect the onset of acoustic energy signal 18 at a unique time t (also referenced as time of arrival) for each transducer 23 in the array. Processor 22 can be used to map the time of arrival and use geometrical analysis (such as triangulation or more complex three-dimensional analysis) to pinpoint the location of any defects in the test sample analogous to that employed with ultrasonic transducers. Alternately, each transducer 23 in array 32 may detect the acoustic energy signal 18 at a unique position in the array. Processor 32 may perform a desired mathematical technique, such as integration of energy, maximum energy, FFT, and the like, and subsequently display a two dimensional or three-dimensional graphical image representative of the geometrical distribution. Such a graphical image representation may be analyzed for geometrical distortions or observed over time for changes in the graphical representation.

Figure 6:
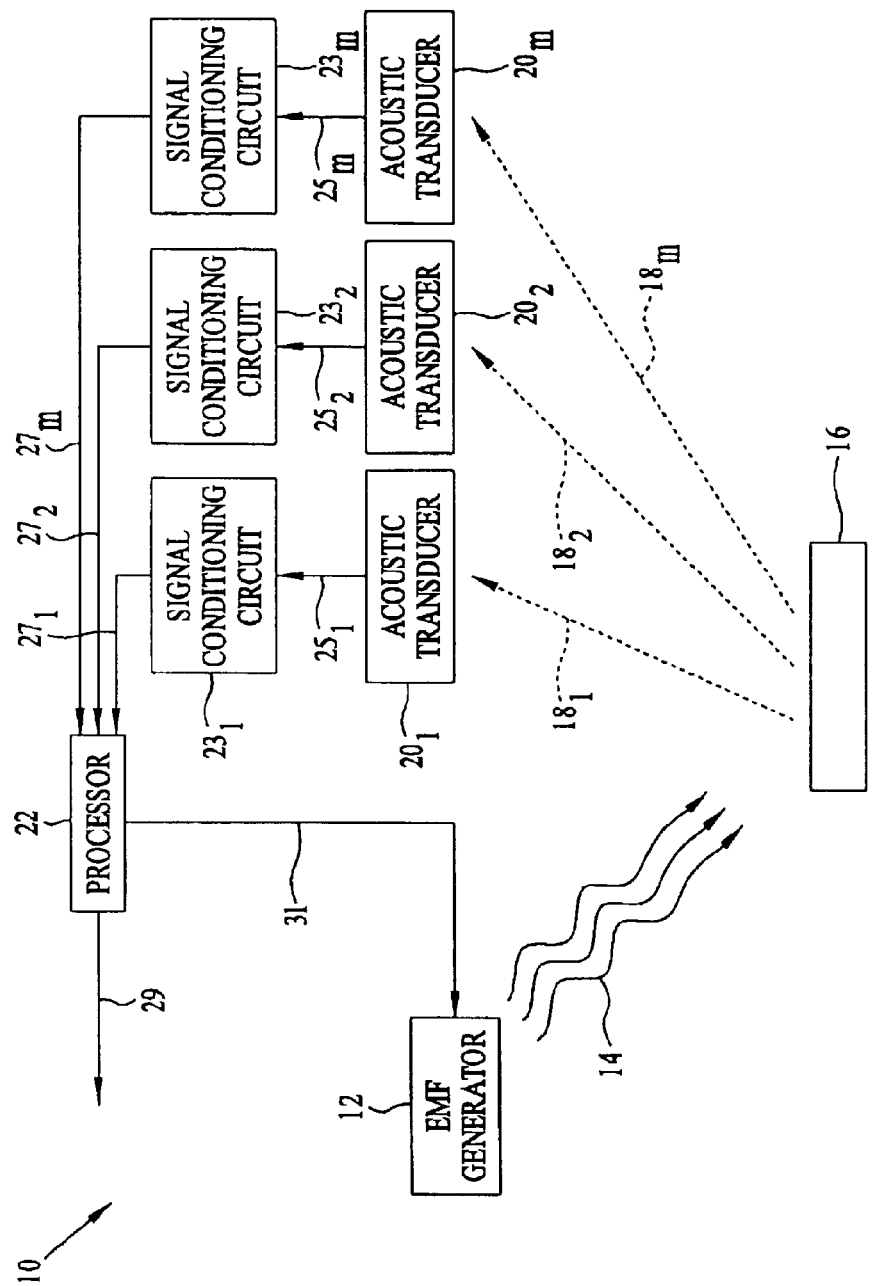
FIG. 6 shows an embodiment of the nondestructive acoustic emission testing system of FIG. 1 that employs multiple acoustic energy sensors for determining the time of arrival of acoustic signals from an acoustic source.

In another embodiment of nondestructive acoustic emission testing system 10, and as shown in FIG. 6, processor 22 may implement a mathematical technique implemented by a suitable software routine that uses the time difference of arrival of multiple acoustic signals $18_1$, $18_2$, $18_3$, ... $18_m$ from test sample 16 to spatially distinct acoustic transducers $20_1$, $20_2$, ... $20_m$ to localize the position of any defect that may be present in test sample 16, where m is a positive integer. Each of acoustic transducers $20_1$, $20_2$, ... $20_m$, is positioned at a unique distance from a position within test sample 16, where such position may be coincident with a defect or non-homogenous characteristic within the test sample. Therefore, acoustic energy signals $18_1$, $18_2$, ... $18_m$ require different transit times in order to propagate from such position to the acoustic transducers $20_1, 20_2, \ldots 20_m$. In operation, processor 22 generates an output signal 31 and initiates an internal clock which determines the approximate time at which each of acoustic signals $18_1, 18_2, \ldots 18_m$ reach acoustic transducers $20_1, 20_2, 20_m$, respectively. Output signal causes electromagnetic wave generator 12 to generate electromagnetic energy 14. Each of acoustic transducers $20_1, 20_2, \ldots 20_m$ generates a first output signal $25_1, 25_2, 25_m$, respectively, which undergo signal conditioning. First output signal $25_1, 25_2, \ldots 25_m$, undergo signal conditioning and are transformed by signal conditioning circuits $23_1, 23_2, 23_m$ into output signals $27_1, 27_2, \ldots 27_m$, respectively, that are provided to processor 22 for analysis. The speed of output signal 31, electromagnetic energy 14, signals $25_1, 25_2, \ldots 25_m$, and $27_1, 27_2, \ldots 27_m$, are generally in the range of about $3 \times 10^8$ m/s, where the speed of acoustic energy signal $18_1, 18_2, \ldots 18_m$, is generally less than about 400 m/s. Therefore, the transit times of signals $31, 25_1, 25_2, \ldots 25_m$, and $27_1, 27_2, 27_m$, which are generally electrical signals, and of electromagnetic energy 14 may be ignored in determining a very good approximation for the time of arrival of acoustic energy signals $18_1, 18_2, \ldots 18_m$ from test sample 16 to the acoustic transducers $20_1, 20_2, \ldots 20_m$ FIG. 6 shows three each of acoustic transducers $20_i$ and signal conditioning circuits $23_i$, where i is a positive integer index from 1 to m, by way of example only. The time of arrival is the time required for an acoustic energy signal to propagate from a specific position within the test sample 16 that may be coincident with a defect or non-homogenous characteristic to an acoustic energy transducer. It is to be understood that acoustic emission testing system 10 may include any number of acoustic transducers and signal conditioning circuits as may be required to suit the needs of a particular application.

Obviously, many modifications and variations of the invention are possible in light of the above teachings. It is therefore to be understood that within the scope of the appended claims, the invention may be practiced otherwise than as specifically described.

We claim:

1. A nondestructive testing system comprising:
   a continuous wave electromagnetic wave generator;
   a sensor acoustically coupled to a test sample for producing a first output signal;
   a data processor for comparing said first output signal to a reference, said data processor producing a second output signal representing a change in the corrosion of said test sample.

2. A system according to claim 1 wherein said test sample is substantially enclosed by a waveguide.

3. A system according to claim 1 wherein said sensor is acoustically coupled to said test sample through an acoustic propagating medium.

4. A nondestructive testing system comprising:
   a pulsed wave electromagnetic wave generator;
   a sensor acoustically coupled to a test sample for producing a first output signal;
   a data processor for comparing said first output signal to a reference, said data processor producing a second output signal representing a change in the corrosion of said test sample.

5. A system according to claim 4 wherein said test sample is substantially enclosed by a waveguide.

6. A system according to claim 4 wherein said sensor is acoustically coupled to said test sample through an acoustic propagating medium.

* * * * *